United States Patent
Ni et al.

(10) Patent No.: US 6,610,829 B2
(45) Date of Patent: Aug. 26, 2003

(54) HUMAN EXTRACELLULAR MATRIX-1

(75) Inventors: Jian Ni, Rockville, MD (US); Ping Feng, Gaithersburg, MD (US); Patrick J. Dillon, Carlsbad, CA (US); Reiner L. Gentz, Silver Spring, MD (US); Joseph Merregaert, Antwerp (BE); Patrick Smits, Antwerp (BE)

(73) Assignees: Unversity of Antwerp, Wilrijk (BE); Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/854,549

(22) Filed: May 15, 2001

(65) Prior Publication Data

US 2001/0034334 A1 Oct. 25, 2001

Related U.S. Application Data

(63) Continuation of application No. 09/007,105, filed on Jan. 14, 1998, now abandoned.
(60) Provisional application No. 60/050,113, filed on Jun. 18, 1997, and provisional application No. 60/035,711, filed on Jan. 16, 1997.

(51) Int. Cl.[7] .................................................. C07K 1/00
(52) U.S. Cl. ........................ 530/350; 530/300; 435/7.1; 536/23.1
(58) Field of Search ................................ 530/350, 300; 435/7.1; 536/23.1

(56) References Cited

U.S. PATENT DOCUMENTS

| | | | |
|---|---|---|---|
| 5,872,234 A | 2/1999 | Bandman et al. | 536/23.1 |
| 6,303,765 B1 | 10/2001 | Bandman et al. | 536/23.1 |

FOREIGN PATENT DOCUMENTS

| | | |
|---|---|---|
| WO | WO 97/22623 | 6/1997 |
| WO | WO 97/35976 | 10/1997 |
| WO | WO 00/55633 A2 | 9/2000 |

OTHER PUBLICATIONS

U.S. patent application Ser. No. 09/912,293, Rosen et al.
Johnson, et al., "Characterization of human extracellular matrix protein 1 gene within the pyncnodysostosis." E.M.B.L. Database Accession No: U65932, Aug. 13, 1996.
Genbank Accession No. R83319, "yp82e01.s1 Soares fetal liver spleen 1NFLS Homo sapiens cDNA clone IMAGE:193944 3', mRNA sequence," Hillier et al., Aug. 4, 1995.
Genbank Accession No. R98765, "yq67d11.s1 Soares fetal liver spleen 1 NFLS Homo sapiens cDNA clone Image:200853 3', mRNA sequence," Hillier et al., Sep. 13, 1995.
Genbank Accession No. N71368, "za31b08.s1 Soares fetal liver spleen 1 NFLS Homo sapiens cDNA clone IMAGE:294135 3', mRNA sequence," Hillier et al., Mar. 14, 1996.
Genbank Accession No. N71317, "za30b08.s1 Soares fetal liver spleen 1 NFLS Homo sapiens cDNA clone IMAGE:294039 3', mRNA sequence," Hillier et al., Mar. 14, 1996.
Genbank Accession No. H66729, "yr83e09.s1 Soares fetal liver spleen 1 NFLS Homo sapiens cDNA clone IMAGE:211912 3', mRNA sequence," Hillier et al., Oct. 18, 1995.
Genbank Accession No. R62808, "yi11c04.s1 Soares placenta Nb2HP Homo sapiens cDNA clone IMAGEL:138918 3', mRNA sequence," Hillier et al., May 26, 1995.
Genbank Accession No. H66472, "yu51h12.s1 Soares fetal liver spleen 1NFLS Homo sapiens cDNA clone IMAGE:229703 3', mRNA sequence," Hillier et al., Oct. 18, 1995.
Fuchs, E. (1990) "Epidermal differentiation." Current Opinion in Cell Biology 2:1028–1035.
Fuchs, E. (1990) "Epidermal differentiation: the bare essentials." J. Cell Biol. 111(6/Pt.2):2807–2814.
Backendorf et al. (1992) "A common origin for cornified envelope proteins?" Nature Genetics 2:91.
Steinert et al. (1991) "Glycine loops in proteins: their occurrence in certain intermediate filament chains, loricrins and single–stranded RNA binding proteins" Int. J. Macromol. 13(3)130–139.
Volz et al. (1993) "Physical mapping of a functional cluster of epidermal differentiation genes on chromosome iq21."Genomics 19:92–99.
Johnson et al., The 46th annual Meeting og the American Society of Human Genetics, San Francisco, CA; Abstract No. 2316 (1996).
Genbank Accession No. C01851 "HUMGS0003821 Human adult (K.Okubo) Homo sapiens cDNA, mRNA sequence." Okubo,K. (1995).

(List continued on next page.)

Primary Examiner—Christopher S. F. Low
Assistant Examiner—Hope A. Robinson
(74) Attorney, Agent, or Firm—Human Genome Sciences, Inc.

(57) ABSTRACT

A human ECM-1 polypeptide and DNA (RNA) encoding such polypeptide and a procedure for producing such polypeptide by recombinant techniques is disclosed. Also disclosed are methods for utilizing such polypeptide for stimulating the differentiation in growth of osteoblasts and osteoclasts, which may be used to promote the healing of bone fractures and de novo bone formation, for osteoporosis, for and to promote angiogenesis. Antagonists to the polypeptide of the present invention are also disclosed which may be utilized to treat osteodystrophy, osteohypertrophy, osteoma, osteoblastoma and cancers. Diagnostic assays for identifying mutations in nucleic acid sequence encoding a polypeptide of the present invention.

70 Claims, 7 Drawing Sheets

OTHER PUBLICATIONS

Genbank Accession No. R83413 "yp82d08.r1 Soares fetal liver spleen 1NFLS Homo sapiens cDNA clone IMAGE:193935 5', mRNA sequence" Hillier et al., Aug. 04, 1995.

Genbank Accession No. H68980 "yr85h05.r1 Soares fetal liver spleen 1NFLS Homo sapiens cDNA clone IMAGE:212121 5', mRNA sequence." Hillier et al., Oct. 19, 1995.

Genbank Accession No. H90991 "yu89a03.r1 Soares fetal liver spleen 1NFLS Homo sapiens cDNA clone IMAGE:240940 5', mRNA sequence." Hillier et al., Nov. 28, 1995.

Genbank Accession No. W41040 "mc41h06.r1 Soares mouse p3NMF19.5 Mus musculus cDNA clone IMAGE:351131 5' similar to gb:L33416 Mouse (MOUSE); mRNA sequence." Hillier et al., Sep. 11, 1996.

Genbank Accession No. H66728, "yr83e09.s1 Soares fetal liver spleen 1NFLS Homo sapiens cDNA clone IMAGE:211912 3', mRNA sequence," Hillier et al., Oct. 18, 1995.

Genbank Accession No. H68887 "yr85h05.s1 Soares fetal liver spleen 1NFLS Homo sapiens cDNA clone IMAGE:212121 3', mRNA sequence." Hillier et al., Oct. 19, 1995.

Genbank Accession No. H66471, "yu51h12.s1 Soares fetal liver spleen 1NFLS Homo sapiens cDNA clone IMAGE:229703 3', mRNA sequence," Hillier et al., Oct. 18, 1995.

Genbank Accession No. T71394 "yd35b08.r1 Soares fetal liver spleen 1NFLS Homo sapiens cDNA clone IMAGE:110199 5', mRNA sequence." Hillier et al., Mar. 15, 1995.

Genbank Accession No. R62857, "yi11c04.s1 Soares placenta Nb2HP Homo sapiens cDNA clone IMAGE:138918 3', mRNA sequence," Hillier et al., May 26, 1995.

Genbank Accession No. 68186 "Human extracellular matrix protein 1 mRNA, complete cds." Smits, et al. Dec. 04, 1997.

Genbank Accession No. 68187 "Human extracellular matrix protein 1 mRNA, alternative splice variant, complete cds." Smits, et al. Dec. 04, 1997.

Genbank Accession No. 65933 "Human extracellular matrix protein 1 (ECM1) gene, exon 1." Johnson et al., Aug. 02, 1996.

Genbank Accession No. 65934 "Human extracellular matrix protein 1 (ECM1) gene, exon 2 through 6." Johnson et al., Aug. 02, 1996.

Genbank Accession No. 65935 "Human extracellular matrix protein 1 (ECM1) gene, exon 7." Johnson et al., Aug. 02, 1996.

Genbank Accession No. 65966 "Human extracellular matrix protein 1 (ECM1) gene, exon 8." Johnson et al., Aug. 02, 1996.

Genbank Accession No. 65937 "Human extracellular matrix protein 1 (ECM1) gene, exon 9." Johnson et al., Aug. 02, 1996.

Genbank Accession No. 65938 "Human extracellular matrix protein 1 (ECM1) gene, exon 10 and complete cds." Johnson et al., Aug. 02, 1996.

Bhalero, J. et al., "Molecular cloning, characterization, and genetic mapping of the cDNA coding for a novel secretory protein of mouse." J. Biol. Chem., 270: 16385–16394 (1995).

Smits, P. et al., "The human extracellular matrix gene 1(ECM1): genomic structure, cDNA cloning, expression, pattern and chromosomal localization." The 25th European Symposium on Calcified Tissues, 20:4S (1997).

Smits, et al. "The human extracellular matrix gene 1 (ECM1): genomic structure, cDNA cloning, expression pattern, and chromosomal localization" Genomics 45 (3), 487–495 (1997).

Johnson et al., "Characterization of the human extracellular matrix protein 1 gene on chromosome 1q21" Matrix Biol. 16 (5), 289–292 (1997).

Figure 1A

```
1    ACAACCGTAACAGCCACCAGACAAGCTTCAGTGGCCCCTTCACATCCAGACTTGCCT     60

61   GAGAGGACCCACCTCTGAGTGTCCAGTTGGTCCAGTTGCCCCAGGATGGGGACCACAGCCAG   120
1                                                M  G  T  T  A  R    6

121  AGCAGCCTTGGTCTCTTGACCTATTTGGCTGTGTTGCTTCTGAGGGAGGCTTCAC         180
7    A  A  L  V  L  T  Y  L  A  V  A  S  A  A  S  E  G  G  F  T    26
                                           ↑

181  GGCTACAGGACAGAGGCAGCTGAGGCCAGACACTTTCAAGAAGTTGGCTACGCAGCTCC    240
27   A  T  G  Q  R  Q  L  R  P  E  H  F  Q  E  V  G  Y  A  A  P    46

241  CCCCTCCCCACCCCTATCCCCGAAGCCTCCCCTGACTCCTCTCAGCATGG            300
47   P  S  P  P  L  S  R  S  L  P  M  D  H  P  D  S  S  Q  H  G    66

301  CCCTCCCCTTTGAGGGACAGAGTCAAGTGCAGCCCCCTCCTCCAGGAGGCCACCCCTCT    360
67   P  P  F  E  G  Q  S  Q  V  Q  P  P  P  S  Q  E  A  T  P  L    86
```

Figure 1B

```
361  CCAACAGGAAAAGCTGCTACCTGCCCAACTCCCCTGCTGAAAAGGAAGTGGGTCCCCCTCT  420
 87   Q  Q  E  K  L  L  P  A  Q  L  P  A  E  K  E  V  G  P  P  L   106

421  CCCTCAGGAAGCTGTCCCCCTCCAAAAGAGCTGCCCTCTCCAGCACCCCAATGAACA     480
107   P  Q  E  A  V  P  L  Q  K  E  L  P  S  L  Q  H  P  N  E  Q   126

481  GAAGGAAGGAACGCCAGCTCCATTTGGGACCAGAGCCATCCAGAACCTGAGTCCTGGAA   540
127   K  E  G  T  P  A  P  F  G  D  Q  S  H  P  E  P  E  S  W  N   146

541  TGCAGCCCAGCACTGCCAACAGGACCGGTCCCAAGGGGCTGGGGCCACCGGCTGGATGG   600
147   A  A  Q  H  C  Q  Q  D  R  S  Q  G  G  W  G  H  R  L  D  G   166

601  CTTCCCCCCTGGGCGCCCTTCTCCAGACAATCTGAACCAAATCTGCCTTCCTAACCGTCA   660
167   F  P  P  G  R  P  S  P  D  N  L  N  Q  I  C  L  P  N  R  Q   186

661  GCATGTGGTATATGGTCCCTGGAACCTACCACAGTCCAGTCCCACCTCACTCGCCA      720
187   H  V  V  Y  G  P  W  N  L  P  Q  S  S  Y  S  H  L  T  R  Q   206
```

Figure 1C

```
721  GGGTGAGACCCTCAATTTCCTGGAGATTGGATATTCCCGTCTGCCACTGCCGCAGCCA  780
207  G  E  T  L  N  F  L  E  I  G  Y  S  R  C  C  H  C  R  S  H   226

781  CACAAACCGCCTAGAGTGTGCCAAACTTGTGGAGGAAGCTATGAGCCGCTTCTGTGAG  840
227  T  N  R  L  E  C  A  K  L  V  E  E  A  M  S  R  F  C  E   246

1141  R  C  C  R  Q  G  N  H  T  C  T  W  K  A  W  E  D  T  L       1200
 347  TGACAAATACTGTGACCGGGAGTATGCTGTGAAGACCCACCACTGTGTTGCCGCCA       366
         *

1201  D  K  Y  C  D  R  E  Y  A  V  K  T  H  H  H  L  C  C  R  H   1260
 367  CCCTCCCAGCCCTACTCGGGATGAGTGCTTTGCCCGTCGGGCTCCTTACCCCAACTATGA   386

1261  P  P  S  P  T  R  D  E  C  F  A  R  R  A  P  Y  P  N  Y  D   1320
 387  CCGGGACATCTTGACCATTGACATCAGTCGAGTCACCCCCAACCTCATGGGCCACCTCTG   406

1321  R  D  I  L  T  I  D  I  S  R  V  T  P  N  L  M  G  H  L  C   1380
 407  TGGAAACCAAAGAGTTCTCACCAAGCATAAAACATATTCCTGGGCTGATCCACAACATGAC   426

```
1441  TGCCCGCTGCTGTGACCTGCCATTTCCAGAAACAGGCCTGCTGTGCAGAGGAGGAGAAATT  1500
447    A  R  C  C  D  L  P  F  F  P  E  Q  A  C  C  A  E  E  E  K  L   466

1501  AACCTTCATCAATGATCTGTGTGGTCCCCGACGTAACATCTGGCGAGACCCTGCCCCTCTG  1560
467    T  F  I  N  D  L  C  G  P  R  R  N  I  W  R  D  P  A  L  C    486

1561  CTGTTACCTGAGTCCTGGGATGAACAGGTCAACTGCTTCAACATCAATTATCTGAGGAA  1620
487    C  Y  L  S  P  G  D  E  Q  V  N  C  F  N  I  N  Y  L  R  N    506

1621  CGTGGCTCTAGTGTCTGGAGACACTGAGAACGCCAAGGGCCAGGGGAGCAGGGCTCAAC  1680
507    V  A  L  V  S  G  D  T  E  N  A  K  G  Q  G  E  Q  G  S  T    526

1681  TGGAGGAACAAATATCAGCTCCACCTCTGAGCCCAAGGAAGAATGAGTCACCCCAGAGCC  1740
527    G  G  T  N  I  S  S  T  S  E  P  K  E  E  *                    541
              *

1741  CTAGAGGGTCAGATGGGGGAACCCCACCCTGCCCCATCTGAACACTCATTACACT       1800
```

Figure 1F

1801 AAACACCCTCTTGGAAAAAAAAAAAAAAAAA 1832

Figure 2

```
  1   MGTTARAALVLTYLAVASAASEGGFTATGQRQLRPE....HFQEVGYAAP   46
      |||..||||:|.:||:||||||||:|.|.:||::  ||    |::|||||||
  1   MGTVSRAALILACLALASAASEGAFKASDQREMTPERLFQHLHEVGYAAP   50

47   PSPPLSRSLPMDHPDSSQHGPP.FEGQSQVQPPPSQEATPLQQEKLLPAQ   95
      || | .|.|.:||. .| |:|| ||:|.:||||.|.|..|: :|.: .
 51   PSLPQTRRLRVDHSVTSLHDPPLFEEQREVQPPSSPEDIPVYEEDWPTFL  100

96   LPAEKEVGPPLPQEAVPLQKELPSLQHPNEQKEGTPAP............  133
      |. ...||::||||:|||||  |. | .||||  .|::
101   NPNVDKAGPAVPQEAIPLQKEQPPPQVHIEQKEIDPPAQPQEEIVQKEVK  150

134   ...FGDQSHPEPESWNAAQHCQQDRSQGGWGHRLDGFPPGRPSPDNLNQI  180
      :::|  .|||  .||:|.||||:|  .|.||||||||||||||||||.||
151   PHTLAGQLPPEPRTWNPARHCQQGR.RGVWGHRLDGFPPGRPSPDNLKQI  199

181   CLPNRQHVVYGPWNLPQSSYSHLTRQGETLNFLEIGYSRCCHCRSHTNRL  230
      |||:|||||:|||||||..:||||.||||||||.||.||||||.|||.||||
200   CLPERQHVIYGPWNLPQTGYSHLSRQGETLNVLETGYSRCCPCRSDTNRL  249

231   ECAKLVWEEAMSRFCEAEFSVKTRPHWCCTRQGEARFSCFQEEAPQPHYQ  280
      :|  ||||||:||..||||||||||||||:||   .||.||||||.|||.|.
250   DCLKLVWEDAMTQFCEAEFSVKTRPHLCCRLRGEERFSCFQKEAPRPDYL  299

281   LRACPSHQPDISSGLELPFPPGVPTLDNIKNICHLRRFRSVPRNLPATDP  330
      ||:||  ||  ::|||  :|  ||||:||  ||:||||  |||||.||||||||:
300   LRPCPVHQNGMSSGPQLPFPPGLPTPDNVKNICLLRRFRAVPRNLPATDA  349

331   LQRELLALIQLEREFQRCCRQGNNHTCTWKAWEDTLDKYCDREYAVKTHH  380
      :|||: ||..|| |||||||||||:|||||||||||:||| ||:||.|:||||
350   IQRQLQALTRLETEFQRCCRQGHNHTCTWKAWEGTLDGYCERELAIKTHP  399

381   HLCCRHPPSPTRDECFARRAPYPNYDRDILTIDISRVTPNLMGHLCGNQR  430
      |  ||:.||||.||||||:  |||||||||:|:||||||||||:|||..|
400   HSCCHYPPSPARDECFAHLAPYPNYDRDILTLDLSRVTPNLMGQLCGSGR  449

431   VLTKHKHIPGLIHNMTARCCDLPFPEQACCAEEEKLTFINDLCGPRRNIW  480
      ||.|||:|||||.|||:|| ||||:||||||:|||||.||::||||||| |
450   VLSKHKQIPGLIQNMTVRCCELPYPEQACCGEEEKLAFIENLCGPRRNSW  499

481   RDPALCCYLSPGDEQVNCFNINYLRNVALVSGDTENAKGQGEQGSTGGTN  530
      :||||||| |||:|.|:||||.||||||||||.|||:|.| |||| .| ||:
500   KDPALCCDLSPEDKQINCFNTNYLRNVALVAGDTGNATGLGEQGPTRGTD  549

531   ISSTSEPKEE  540
          .....:.|||
550   ANPAPGSKEE  559
```

HUMAN EXTRACELLULAR MATRIX-1

This application is a continuation of and claims priority under 35 U.S.C. §120 to U.S. application Ser. No. 09/007, 105 now abandoned, filed Jan. 14, 1998, which claims benefit under 35 U.S.C. § 119(e) of U.S. Provisional application Ser. Nos. 60/035,711, filed Jan. 16, 1997 and 60/050, 113, filed Jun. 18, 1997, each of which is hereby incorporated herein by reference in its entirety.

This invention relates to newly identified polynucleotides, polypeptides encoded by such polynucleotides, the use of such polynucleotides and polypeptides, as well as the production of such polynucleotides and polypeptides. The polypeptide of the present invention has been putatively identified as the human homolog of the mouse Extracellular Matrix-1 protein, sometimes hereinafter referred to as "hECM-1." The invention also relates to inhibiting the action of such polypeptides.

BACKGROUND OF THE INVENTION

The process of embryonic bone formation involves the creation of an extracellular matrix that mineralizes during the course of tissue maturation. This matrix is subject to constant remodeling during the lifetime of an individual, through the combined actions of osteoblasts and osteoclasts. A careful balance of matrix formation and resorption must be maintained because perturbations can result in various bone disorders.

The extracellular matrix of bone consists of two phases, an organic phase and a mineral phase. The organic phase consists primarily of the collagen type I fibrils that are associated with a number of noncollagenous matrix proteins. Interest in the noncollagenous proteins of the bone has been greatly stimulated since Urist first demonstrated that demineralized bone extracts could induce ectopic bone formation (Urist, M. R., *Science,* 150:893–899 (1965)). Noncollagenous proteins of bone are now believed to be involved in mineralization as well as the local regulation of bone cell function (Heinegard, D. and Oldberg, A., *Connective Tissue and Its Heritable Disorders* (Royce, P. M. and Steinmann, B., EDS), pages 189–209, Wiley-Liss, New York (1993), and Von der Mark, K. and Goodman, S., id.). In the past few years, a number of noncollagenous proteins of bone have been isolated and characterized; among these are osteocalcin, osteopontin, osteonectin and bone sialoprotein (Heinegard, D. and Oldberg, A., *FASEB J.,* 3:2042–2051 (1985)).

A clonal osteogenic cell line (MN7) from bone marrow stroma of the adult mouse has been established (Mathieu, E., et al., *Calcif. Tissue Int.,* 50:362–371 (1992)). These cells, under appropriate conditions, undergo typical osteoblastic differentiation in vitro and are able to form a mineralized extracellular matrix (Mathieu, E. and Merregaert, J., *J. Bone Miner. Res.,* 9:183–192 (1994)).

A cDNA coding for a novel secretory protein of mouse (p85), has been cloned, characterized and genetically mapped (Bhalerao, J., et al., *J. Biol. Chem.,* 270 (27) :16385–16394 (1995)). The full-length cDNA contains an open reading frame of 1677 bp encoding a protein of 559 amino acids. The clone contains a hydrophobic signal peptide characteristic of a secreted protein. The message of 1.9 kb is expressed in various tissues, such as liver, heart, lungs, etc., whereas a splice variant was present in embryonic cartilage in skin. This gene p85, called Ecm1 for extracellular matrix protein 1, maps on chromosome 3 of mouse in a region containing several loci involved in skin development disorders.

The polypeptide of the present invention has highest amino acid sequence homology to growth factor Ecm1.

SUMMARY OF THE INVENTION

In accordance with one aspect of the present invention, there is provided a novel mature polypeptide, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding a polypeptide of the present invention including mRNAs, cDNAs, genomic DNAs as well as analogs and biologically active and diagnostically or therapeutically useful fragments thereof.

In accordance with another aspect of the present invention there is provided an isolated nucleic acid molecule encoding a mature polypeptide expressed by the DNA contained in ATCC Deposit No. 97302.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process for utilizing such polypeptide, or polynucleotide encoding such polypeptide for therapeutic purposes, for example, to stimulate osteoblast and osteoclast differentiation and growth, which may be utilized to treat bone disorders and promote bone formation for healing of bone fractures and treatment of osteoporosis and osteogenesis imperfecta, and to stimulate angiogenesis, which may be utilized to revascularize injured tissue.

In accordance with yet a further aspect of the present invention, there are provided antibodies against such polypeptides.

In accordance with another aspect of the present invention, there are provided hECM-1 agonists which mimic hECM-1 and bind to the hECM-1 receptors and antagonists against such polypeptides, which may be used to inhibit the action of such polypeptides. The agonists may be employed to treat disease conditions related to an underexpression of the ECM-1 polypeptide and the antagonists may be employed to treat disease conditions related to an overexpression of such polypeptide. Such disease conditions include, for example, osteodystrophy, osteohypertrophy, osteoma, osteopetrusis, osteoporosis, osteoblastoma, and cancer.

In accordance with yet a further aspect of the present invention, there is also provided nucleic acid probes comprising nucleic acid molecules of sufficient length to specifically hybridize to a nucleic acid sequence of the present invention.

In accordance with still another aspect of the present invention, there are provided diagnostic assays for detecting diseases or susceptibility to diseases related to mutations in the nucleic acid sequences encoding a polypeptide of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIGS. 1A–F are an illustration of the CDNA (SEQ ID NO:1) and corresponding deduced amino acid sequence (SEQ ID NO:2) of the polypeptide of the present invention. The underlined portion is indicative of a putative leader sequence. Sequencing was performed using a 373 automated DNA sequencer (Applied Biosystems, Inc.).

FIG. 2 is an amino acid sequence comparison between the polypeptide of the present invention (SEQ ID NO:2) (top line) and murine Ecm1 (SEQ ID NO:7) (bottom line).

DETAILED DESCRIPTION OF THE INVENTION

In accordance with an aspect of the present invention, there is provided an isolated nucleic acid (polynucleotide) which encodes for the mature polypeptide having the deduced amino acid sequence of FIGS. 1A–F (SEQ ID NO:2).

The polynucleotide of this invention was discovered in a cDNA library derived from a human tumor pancreas. It is structurally related to the murine Ecm1. It contains an open reading frame encoding a protein of 540 amino acid residues of which the first 19 amino acids residues are the putative leader sequence (underlined in FIGS. 1A–F) such that the mature protein comprises 521 amino acids (amino acids 20–540 in FIGS. 1A–F). As can be seen in FIG. 2, the protein exhibits the highest degree of homology to murine Ecm1 at the amino acid level with 69.4% identity and 81.3% similarity over the entire amino acid stretch. The gene of the present invention exhibits the highest degree of homology at the nucleotide level also to murine Ecm1 with 80% identity and 80% similarity over the entire nucleotide sequence.

In accordance with another aspect of the present invention there are provided isolated polynucleotides encoding a mature polypeptide expressed by the DNA contained in ATCC Deposit No. 97302, deposited with the American Type Culture Collection ("ATCC"), 10801 University Boulevard, Manassas, Va. 20110-2209, USA, on Sep. 25, 1995. The deposited material is a plasmid that contains the full-length hECM-1 cDNA inserted into a pBluescript SK(–) vector (Stratagene, La Jolla, Calif.).

The deposit has been made under the terms of the Budapest Treaty on the International Recognition of the Deposit of Micro-organisms for purposes of Patent Procedure. The strain will be irrevocably and without restriction or condition released to the public upon the issuance of a patent. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are controlling in the event of any conflict with any description of sequences herein. A license may be required to make, use or sell the deposited materials, and no such license is hereby granted. References to "polynucleotides" throughout this specification includes the DNA of the deposit referred to above.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–F (SEQ ID NO:1) or may be a different coding sequence which coding sequence, as a result of the redundancy or degeneracy of the genetic code, encodes the same mature polypeptide as the DNA of FIGS. 1A–F (SEQ ID NO:1).

The polynucleotide which encodes for the mature polypeptide of FIGS. 1A–F (SEQ ID NO:2) may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–F (SEQ ID NO:2). The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–F (SEQ ID NO:2) as well as variants of such polynucleotides which variants encode for a fragment, derivative or analog of the polypeptide of FIGS. 1A–F (SEQ ID NO:2). Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–F (SEQ ID NO:1). As is known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 85%, preferably at least 90%, and more preferably at least 95%, 96%, 97%, 98%, or 99% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A–F (SEQ ID NO: 1).

Alternatively, the polynucleotide may have at least 20 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least an 85% identity, preferably at least a 90% identity and more preferably at least a 95%, 96%, 97%, 98%, or 99% identity to a polynucleotide which encodes the polypeptide of SEQ ID NO:2 and polynucleotides complementary thereto, as well as portions thereof, which portions have at least 30 consecutive bases and more preferably at least 50 consecutive bases and to polypeptides encoded by such polynucleotides.

The present invention further relates to a polypeptide which has the deduced amino acid sequence of FIGS. 1A–F (SEQ ID NO:2), as well as fragments, analogs and derivatives of such polypeptide.

The terms "fragment," "derivative" and "analog" when referring to the polypeptide of FIGS. 1A–F (SEQ ID NO:2), means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–F (SEQ ID NO:2) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Also preferred in this aspect of the invention are fragments characterized by structural or functional attributes of hECM-1. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of hECM-1.

Certain preferred regions in these regards include, but are not limited to, regions of the aforementioned types identified by analysis of the amino acid sequence set out in FIGS. 1A–F. Such preferred regions include Garnier-Robson alpha-regions, beta-regions, turn-regions and coil-regions, Chou-Fasman alpha-regions, beta-regions and turn-regions, Kyte-Doolittle hydrophilic regions and hydrophilic regions, Eisenberg alpha and beta amphipathic regions, Karplus-Schulz flexible regions, Emini surface-forming regions and Jameson-Wolf high antigenic index regions.

Particularly preferred polypeptides comprise the entire amino acid sequence shown in FIGS. 1A–F (SEQ ID NO:2) except the amino terminal methionine. Accordingly, the present invention provides a polypeptide comprising an amino acid sequence at least 95% identical to the amino acid sequence shown in FIGS. 1A–F lacking the amino terminal methionine. Polynucleotides encoding such polypeptides are also provided.

Also forming part of the invention are polypeptides comprising the amino acid sequence of a splice variant of hECM-1, sometimes hereinafter "hECM-1-SV1". hECM-1-SV1 is missing 375 nucleotides which code for 125 amino acids. The region of hECM-1-SV1 missing from the hECM-1 cDNA is shown in FIGS. 1A–F as a shaded region containing nucleotides 812–1186. The hECM-1-SV1 nucleotide sequence is set out as SEQ ID NO:8. The corresponding hECM-1 amino acid sequence is shown as SEQ ID NO:9. Accordingly, the invention provides polypeptides comprising an amino acid sequence at least 95% identical to the amino acid sequence of hECM-1-SV1. Polynucleotides encoding such polypeptides are also provided.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 80% similarity (preferably at least 80% identity) to the polypeptide of SEQ ID NO:2 and more preferably at least 90% similarity (more preferably at least 90% identity) to the polypeptide of SEQ ID NO:2 and still more preferably at least 95%, 96%, 97%, 98%, and 99% similarity (still more preferably at least 95%, 96%, 97%, 98%, or 99% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli. lac* or *trp*, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimurium*; fungal cells, such as yeast; insect cells such as *Drosophila S2* and *Spodoptera Sf9*; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); pTRC99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

Human ECM-1 is thought to stimulate osteogenesis and angiogenesis (particularly in embryonic development). Therefore, given the activities modulated by hECM-1, it is readily apparent that a substantially altered (increased or decreased) level of expression of hECM-1 in an individual compared to the standard or "normal" level produces pathological conditions such as those described below. It will also be appreciated by one of ordinary skill that, since the hECM-1 protein of the invention is translated with a leader peptide suitable for secretion of the mature protein from the cells which express hECM-1, when hECM-1 protein (particularly the mature form) is added from an exogenous source to cells, tissues or the body of an individual, the protein will exert its modulating activities on any of its target cells of that individual. Therefore, it will be appreciated that conditions caused by a decrease in the standard or normal level of hECM-1 activity in an individual, particularly disorders relating to fetal development, osteogenesis and angiogenesis, can be treated be administration of hECM-1 protein. Thus, the invention also provides a method of treatment of an individual in need of an increased level of hECM-1 activity comprising administering to such an individual a pharmaceutical composition comprising an amount of an isolated hECM-1 polypeptide of the invention, particularly a mature form of the hECM-1 protein of the invention, effective to increase the hECM-1 activity level in such an individual.

More in particular, the hECM-1 gene and gene product of the present invention may be employed to promote osteoblast and osteoclast differentiation and growth, as well as mineralization of bone. Accordingly, hECM-1 may be employed to promote bone growth, to treat osteoporosis, osteogenesis imperfecta and facilitate the healing of fractures.

hECM-1 gene and gene product of the present invention may also be employed to promote angiogenesis, especially in early fetal development and, for example, in revascularization of transplanted or injured tissue, for example, to stimulate the growth of transplanted tissue where coronary bypass surgery is performed. An hECM-1 polypeptide may also be employed to stimulate wound healing, particularly to re-vascularize damaged tissues or where new capillary angiogenesis is desired. An hECM-1 polypeptide may be employed to treat full-thickness wounds such as dermal ulcers, including pressure sores, venous ulcers, and diabetic ulcers. In addition, hECM-1 polypeptides may be employed to treat full-thickness burns and injuries where a skin graft or flap is used to repair such burns and injuries and also may be employed for use in plastic surgery, for example, for the repair of lacerations from trauma and cuts in association with surgery. hECM-1 may also be used to treat ischemia.

Along these same lines, an hECM-1 polypeptide may be employed to induce growth of damaged bone, peridontium or ligament tissue. Neo-vascularization is very important in fracture repair, as evidenced by blood vessel development at the site of bone injuries. An hECM-1 polypeptide may also be employed for regeneration supporting tissues of the teeth, including cementum and periodontal ligament, that have been damaged by disease and trauma.

Since angiogenesis is important in keeping wounds clean and non-infected, an hECM-1 polypeptide may be employed in association with surgery and following the repair of cuts. It may also be employed for the treatment of abdominal wounds where there is a high risk of infection.

An hECM-1 polypeptide may be employed for the promotion of endothelialization in vascular graft surgery. In the case of vascular grafts using either transplanted or synthetic material, an hECM-1 polypeptide can be applied to the surface of the graft or at the junction to promote the growth of vascular endothelial cells. An hECM-1 polypeptide may also be employed to repair damage of myocardial tissue as the result of myocardial infarction and may also be employed to repair the cardiac vascular system after ischemia. Further, an hECM-1 polypeptide may also be employed to treat damaged vascular tissue as a result of coronary artery disease and peripheral and CNS vascular disease.

An hECM polypeptide may also be employed for vascular tissue repair, for example, that required during arteriosclerosis and following balloon angioplasty where vascular tissues are damaged and may also be employed to coat artificial prostheses or natural organs which are to be transplanted in the body to minimize rejection of the transplanted material and to stimulate vascularization of the transplanted materials.

An hECM-1 polypeptide may be employed as a vascularizing agent to impregnate or coat implant materials for the timed release of pharmaceutical agents, as for example, when such implants are employed subcutaneously.

The polynucleotides and polypeptides of the present invention may also be employed as research reagents and materials for discovery of treatments and diagnostics to human disease.

This invention provides a method for identification of the receptor for hECM-1. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to hECM-1, and a cDNA library created from this RNA is divided into pools and used to transfect COS cells or other cells that are not responsive to hECM-1. Transfected cells which are grown on glass slides are exposed to labeled hECM-1, which may be labeled by a variety of means including iodination or inclusion of a recognition site for a site-specific protein kinase. Following fixation and incubation, the slides are subjected to auto-radiographic analysis. Positive pools are identified and sub-pools are prepared and re-transfected using an iterative sub-pooling and re-screening process, eventually yielding a single clone that encodes the putative receptor. As an alternative approach for receptor identification, labeled hECM-1 can be photoaffinity linked with cell membrane or extract preparations that express the receptor molecule. Cross-linked material is resolved by PAGE and exposed to X-ray film. The labeled complex containing the ligand-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

This invention provides a method of screening compounds to identify those which enhance (agonists) or block (antagonists) interaction of hECM-1 with its receptor. As an example, a mammalian cell or membrane preparation expressing the hECM-1 receptor is incubated with labeled hECM-1 in the presence of the compound. The ability of the compound to enhance or block this interaction could then be measured. Potential antagonists include an antibody, or in some cases, an oligopeptide, which are specific to an epitope of the hECM-1 polypeptide. Alternatively, a potential antagonist may be a closely related protein which binds to the receptor sites, however, they are inactive forms of the polypeptide and thereby prevent the action of hECM-1 since receptor sites are occupied.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251:1360 (991)), thereby preventing transcription and the production of hECM-1. The antisense RNA oligonucleotide hybridizes to the mRNA in vivo and blocks translation of the MRNA molecule into hECM-1 polypeptide (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of hECM-1.

Potential antagonists include a small molecule which binds to and occupies the active site of the polypeptide thereby making it inaccessible to substrate such that normal biological activity is prevented. Examples of small molecules include but are not limited to small peptides or peptide-like molecules.

The agonists and antagonists may be employed to augment of reduce the biological effects of the polypeptide of the present invention where appropriate in the treatment of osteodystrophy, osteohypertrophy, osteoblastoma, osteopertrusis, osteoporosis, osteoma and osteoblastoma. Antagonists will be particularly useful in the treatment of cancer by inhibiting the angiogenesis of tumors. It is significant in this regard that the deposited cDNA was isolated from cancerous tissue and that hECM-1 is found by immunohistochemical staining in several cancerous tissues.

hECM-1 polypeptide stimulation of neovascular activity may be a significant factor in allowing various cancers to become invasive or metastasize. In addition to invasive cancer, various other animal disorders involve abnormally high neovascular activity. In such cases, antagonists to hECM-1 stimulation of neovascularization may be generally useful in controlling the progression of such conditions.

Potential antagonists include antibodies which bind to hECM-1 polypeptides and effectively eliminate or reduce hECM-1 function. Alternatively, a potential antagonist may be a closely related protein which binds to hECM-1 receptors, but are inactive forms of the polypeptide, thereby preventing the action of a hECM-1 polypeptide. Examples of these antagonists include a negative dominant mutant of a hECM-1 polypeptide, for example, the polypeptide may be mutated such that biological activity is not retained. By binding its receptor, these negative mutants are "dominant" in that it brings about a loss of hECM-1 polypeptide activity, even though some wild-type hECM-1 polypeptides are produced from the other allele.

Another potential hECM-1 antagonist is an antisense construct prepared using antisense technology. Antisense technology can be used to control gene expression through triple-helix formation or antisense DNA or RNA, both of which methods are based on binding of a polynucleotide to DNA or RNA. For example, oligonucleotides complementary to splice junctions are particularly effective antagonists of the expressed product, by having disrupted the mRNA processing events necessary for an active product. A DNA oligonucleotide is designed to be complementary to a region of the gene involved in transcription (triple helix—see Lee et al., Nucl. Acids Res. 6:3073 (1979); Cooney et al., Science 241:456 (1988); and Dervan et al., Science 251:1360 (1991)), thereby preventing transcription and the production of a hECM-1 polypeptide. The antisense RNA oligonucleotide hybridizes to the MRNA in vivo and blocks translation of the mRNA molecule into the hECM-1 polypeptide (Antisense—Okano, J. Neurochem. 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of hECM-1.

Potential hECM-1 antagonists also include small-molecules which bind to and occupy the active site of the polypeptide thereby making the catalytic site inaccessible to substrate such that normal biological activity is prevented. Examples of small molecules include, but are not limited to, small peptides or peptide-like molecules. Small molecules can also act to block transcription and translation by binding to DNA or RNA such that transcription and translation factors cannot bind. For small molecules to function in this system they must be small enough to pass through the cell and nuclear membranes.

The antagonists may also be used to treat inflammation caused by increased vascular permeability. In addition to these disorders, the antagonists may also be used to treat diabetic retinopathy, rheumatoid arthritis and psoriasis.

The antagonists may be employed in a composition with a pharmaceutically acceptable carrier, e.g., as hereinafter described.

The polypeptides of the present invention, and agonists and antagonists, may be employed in combination with a suitable pharmaceutical carrier. Such compositions comprise a therapeutically effective amount of the polypeptide, agonists or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention, or agonists or antagonists, may be employed in conjunction with other therapeutic compounds.

The pharmaceutical compositions may be administered in a convenient manner such as by the oral, topical, parenterally, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The hECM-1 polypeptides and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and b-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the b-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, y-2, y-AM, PA12, T19-14X, VT-19-17-H2, yCRE, yCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the gene of the present invention as a diagnostic. Detection of a mutated form of the gene will allow a diagnosis of a disease or a susceptibility to a disease which results from underexpression of hECM-1.

Individuals carrying mutations in the gene of the present invention may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding hECM-1 can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the polypeptide of the present invention in various tissues since an over-expression of the proteins compared to normal control tissue samples can detect the presence of bone disorders, for example, osteoporosis. Assays used to detect levels of the polypeptide of the present invention in a sample derived from a host are well-known to those of skill in the art and include radioimmunoassays, competitive-binding assays, Western Blot analysis and preferably an ELISA assay. An ELISA assay initially comprises preparing an antibody specific to the hECM-1 antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attached to any of the polypeptide of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of the polypeptide of the present invention present in a given volume of patient sample when compared against a standard curve.

A competition assay may be employed wherein antibodies specific to the polypeptide of the present invention are attached to a solid support and labeled hECM-1 and a sample derived from the host are passed over the solid support and the amount of label detected attached to the solid support can be correlated to a quantity of the polypeptide of the present invention in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988).

The hECM-1 gene of the present invention has been mapped to human chromosome 1q21. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 mg of plasmid or DNA fragment is used with about 2 units of enzyme in about 20 ml of buffer solution. For the purpose of isolating DNA fragments for plasmid construction, typically 5 to 50 mg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 mg of approximately equimolar amounts of the DNA fragments to be ligated.

Unless otherwise stated, transformation was performed as described in the method of Graham, F. and Van der Eb, A., Virology, 52:456–457 (1973).

EXAMPLES

Example 1

Cloning and expression of hECM-1 using the baculovirus expression system

The DNA sequence encoding the full length hECM-1 protein, ATCC # 97302, was amplified using PCR oligonucleotide primers corresponding to the 5' and 3' sequences of the gene:

The 5' primer has the sequence 5' CGGGATCCGCCATC ATGGGGACCACAGCCAG 3' (SEQ ID NO:3) and contains a BamHI restriction enzyme site (in bold) followed by nucleotides resembling an efficient signal for the initiation of translation in eukaryotic cells (Kozak, M., J. Mol. Biol., 196:947–950 (1987) just in front of the initiation codon for translation "ATG" (underlined).

The 3' primer has the sequence 5' GCTCTAGATCCAA-GAGGTGTTTAGTG 3' (SEQ ID NO:4) and contains the cleavage site for the restriction endonuclease XbaI and 18 nucleotides complementary to the 3' non-translated sequence. The amplified sequences were isolated from a 1% agarose gel using a commercially available kit ("Geneclean," BIO 101 Inc., La Jolla, Calif.). The fragment was then digested with the endonucleases BamHI and XbaI and then purified again on a 1% agarose gel. This fragment is designated F2.

The vector pA2 (modification of pVL941 vector, discussed below) is used for the expression of the hECM-1 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa califomica nuclear polyhedrosis virus (AcMNPV) followed by the recognition sites for the restriction endonucleases BamHI and XbaI. The polyadenylation site of the simian virus (SV)40 is used for efficient polyadenylation. For an easy selection of recombinant virus the beta-galactosidase gene from E. coli is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pA2 such as pAc373, pVL941 and pAcIMI (Luckow, V. A. and Summers, M. D., Virology, 170:31–39).

The plasmid was digested with the restriction enzymes BamHI and XbaI and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. E. coli HB101 cells were then transformed and bacteria identified that contained the plasmid (pBachECM-1) with the hECM-1 gene using the enzymes BamHI and XbaI. The sequence of the cloned fragment was confirmed by DNA sequencing.

5 mg of the plasmid pBachECM-1 was co-transfected with 1.0 mg of a commercially available linearized baculovirus ("BaculoGold baculovirus DNA", Pharmingen, San Diego, Calif.) using the lipofection method (Felgner et al. Proc. Natl. Acad. Sci. USA, 84:7413–7417 (1987)).

1 mg of BaculoGold virus DNA and 5 mg of the plasmid pBachECM-1 were mixed in a sterile well of a microtiter plate containing 50 ml of serum free Grace's medium (Life Technologies Inc., Gaithersburg, Md.). Afterwards 10 ml Lipofectin plus 90 ml Grace's medium were added, mixed and incubated for 15 minutes at room temperature. Then the transfection mixture was added drop-wise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus was added to the cells and blue stained plaques were picked with the tip of an Eppendorf pipette. The agar containing the recombinant viruses was then resuspended in an Eppendorf tube containing 200 ml of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-hECM-1 at a multiplicity of infection (MOI) of 2. Six hours later the medium was removed and replaced with SF900 II medium minus methionine and cysteine (Life Technologies Inc., Gaithersburg). 42 hours later 5 mCi of $^{35}$S-methionine and 5 mCi $^{35}$S cysteine (Amersham) were added. The cells were further incubated for 16 hours before they were harvested by centrifugation and the labeled proteins visualized by SDS-PAGE and autoradiography.

The supernatant (1000 ml) containing baculovirus expressed hECM-1 was applied without dilution to an HS-50 column (1.0×10 cm, Perseptive Biosystems) equilibrated with 0.02 M Bis-Tris, pH 6.0, containing 10% glycerol and 0.02 M NaCl (Solvent A) at a flow rate of 8 ml/min. Proteins were then eluted using a gradient from 10% Solvent B (Solvent A containing 2 M NaCl) to 30% B. The pooled peak contained 11 mg of hECM-1 having a purity of greater than 80%.

Example 2
Expression of Recombinant hECM-1 in COS cells

The expression of plasmid, hECM-1 HA is derived from a vector pcDNAI/Amp (Invitrogen) containing: 1) SV40 origin of replication, 2) ampicillin resistance gene, 3) E. coli replication origin, 4) CMV promoter followed by a polylinker region, an SV40 intron and polyadenylation site. A DNA fragment encoding the entire hECM-1 precursor and a HA tag fused in frame to its 3' end was cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37:767, (1984)). The infusion of HA tag to the target protein allows easy detection of the recombinant protein with an antibody that recognizes the HA epitope.

The plasmid construction strategy is described as follows:

The DNA sequence encoding hECM-1, ATCC # 97302, was constructed by PCR using two primers: the 5' primer 5' GCGCGGATCCACCATGGGGACCACAGCCAGA 3' (SEQ ID NO:5) contains a BamHI site followed by 18 nucleotides of hECM-1 coding sequence starting from the initiation codon; the 3' sequence 5' GCGCTCTAGAT-CAAGCGTAGTCTGGGACGTCGTATGGG-TATTCTTCCTTGGGC TC 3' (SEQ ID NO:6) contains complementary sequences to an XbaI site, translation stop codon, HA tag and the last 15 nucleotides of the hECM-1 coding sequence (not including the stop codon). Therefore, the PCR product contains a BamHI site, hECM-1 coding sequence followed by HA tag fused in frame, a translation termination stop codon next to the HA tag, and an XbaI site. The PCR amplified DNA fragment and the vector, pcDNAI/Amp, were digested with BamHI and XbaI restriction enzyme and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant hECM-1, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the hECM-1 HA protein was detected by radio labeling and immunoprecipitation method (E. Harlow, D. Lane, Antibodies: A Laboratory Manual, Cold Spring Harbor Laboratory Press, (1988)). Cells were labeled for 8 hours with $^{35}$m-cysteine two days post transfection. Culture media was then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media were precipitated with an HA specific monoclonal antibody. Proteins precipitated were analyzed on 15% SDS-PAGE gels.

Numerous modifications and variations of the present invention are possible in light of the above teachings and, therefore, within the scope of the appended claims, the invention may be practiced otherwise than as particularly described.

Example 3
Immunohistochemical Detection of hECM-1

Immunohistochemistry using a purified polyclonal antibody (269TP) generated in the rabbit against the human Ecm1 protein was performed on paraffin section of archival formalin fixed material. The material included an adenocarcinoma of the lung, a squamous cell carcinoma of the skin and the esophagus, a basal cell carcinoma of the skin, a chondrosarcoma of the femur, an adenoma of the parathyroid and hyperplastic parathyroid tissue, an oat cell carcinoma of the lung, a ductal carcinoma of the breast and placenta and fetus with a gestational period of 22 weeks. All slides contained tumoral tissue and adjacent normal tissue. Prior to the immunohistochemistry the paraffin slides were deparaffinised and the endogenous peroxidase was abolished. After rinsing the slides in PBS the slides were preincubated with normal goat serum. In the first step the slides were incubated with primary Ecm1 antibody in a dilution of ¹/₂₀ for 30 minutes at room temperature. After rinsing in PBS the slides were then incubated with the second antibody (goat anti-rabbit from DAKA) for 30 minutes and after thorough rinsing in PBS they were labeled in a third step with the peroxidase conjugated streptavidin-biotin complex (DAKO) after which the slides were rinsed once more in PBS. The chromagen used was DAB and a hematoxylin counterstain was performed.

Results

In the chondrosarcoma some chondrocytes in the lesion show faint immunoreactivity in the cytoplasm. In the adenocarcinoma of the lung and in the fetal lung tissue there was also cytoplasmic immunoreactivity in some chondrocytes in the bronchial wall. In the adult there was also some reactivity in serous epithelial cells from the peribronchial glands. In all the other lung structures and in the tumour there was no immunoreactivity. In some of the most superficial cells of the normal squamous epithelium and in the squamous carcinomas in a the skin as well as in the esophagus moderate cytoplasmic immunoreactivity was seen. There is no reactivity in the surrounding normal tissues. There was no immunoreactivity in the hyperplastic parathyroid and in the adenoma of the parathyroid. In the breast carcinoma the neoplastic cells showed cytoplasmic immunoreactivity. There was also immunostaining in myoepithelial cells and in adipocytes. There was no immunoreactivity in the basal cell carcinoma from the skin and in the oatcell carcinoma. With the exception of the chondrocytes in the bronchial wall there was no immunoreactivity in the fetal organs or the placenta and cord.

Example 4
HUVEC Proliferation Assay

HUVEC were seeded in medium supplemented with the rhEcm1 protein to concentrations of 100 ng/ml, 10 ng/ml and 1 ng/ml. As a negative control HUVEC were seeded in medium supplemented with the rhecm1 protein suspension buffer. The proliferation of HUVEC was assessed 18 hours later with Alamar blue reagent (Johnson et al., 1995). The rhEcm1 protein was found to stimulate endothelial cell proliferation in a dose-dependent way. A strong effect was observed with a concentration of 100 ng/ml. The smallest significant effect could still be detected at 10 ng/ml (p<0.01, paired t-test).

SEQUENCE LISTING

<160> NUMBER OF SEQ ID NOS: 9

<210> SEQ ID NO 1
<211> LENGTH: 1832
<212> TYPE: DNA
<213> ORGANISM: Homo sapiens
<220> FEATURE:
<221> NAME/KEY: CDS
<222> LOCATION: (104)..(1726)
<221> NAME/KEY: sig_peptide
<222> LOCATION: (104)..(160)
<221> NAME/KEY: mat_peptide
<222> LOCATION: (161)..(1723)

<400> SEQUENCE: 1

```
acaaccgtaa cagccaccag acaagcttca gtggccggcc cttcacatcc agacttgcct          60
gagaggaccc acctctgagt gtccagtggt cagttgcccc agg atg ggg acc aca         115
                                              Met Gly Thr Thr gcc aga gca gcc ttg gtc ttg acc tat ttg gct gtt gct tct gct gcc         163
Ala Arg Ala Ala Leu Val Leu Thr Tyr Leu Ala Val Ala Ser Ala Ala
-15             -10                 -5                  -1  1 tct gag gga ggc ttc acg gct aca gga cag agg cag ctg agg cca gag         211
Ser Glu Gly Gly Phe Thr Ala Thr Gly Gln Arg Gln Leu Arg Pro Glu
                5               10                  15 cac ttt caa gaa gtt ggc tac gca gct ccc ccc tcc cca ccc cta tcc         259
His Phe Gln Glu Val Gly Tyr Ala Ala Pro Pro Ser Pro Pro Leu Ser
        20                  25                  30 cga agc ctc ccc atg gat cac cct gac tcc tct cag cat ggc cct ccc         307
Arg Ser Leu Pro Met Asp His Pro Asp Ser Ser Gln His Gly Pro Pro
    35                  40                  45 ttt gag gga cag agt caa gtg cag ccc cct ccc tct cag gag gcc acc         355
Phe Glu Gly Gln Ser Gln Val Gln Pro Pro Pro Ser Gln Glu Ala Thr
50                  55                  60                  65 cct ctc caa cag gaa aag ctg cta cct gcc caa ctc cct gct gaa aag         403
Pro Leu Gln Gln Glu Lys Leu Leu Pro Ala Gln Leu Pro Ala Glu Lys
                70                  75                  80 gaa gtg ggt ccc cct ctc cct cag gaa gct gtc ccc ctc caa aaa gag         451
Glu Val Gly Pro Pro Leu Pro Gln Glu Ala Val Pro Leu Gln Lys Glu
```

-continued

```
                      85                      90                      95
ctg ccc tct ctc cag cac ccc aat gaa cag aag gaa gga acg cca gct        499
Leu Pro Ser Leu Gln His Pro Asn Glu Gln Lys Glu Gly Thr Pro Ala
            100                     105                     110 cca ttt ggg gac cag agc cat cca gaa cct gag tcc tgg aat gca gcc        547
Pro Phe Gly Asp Gln Ser His Pro Glu Pro Glu Ser Trp Asn Ala Ala
    115                     120                     125 cag cac tgc caa cag gac cgg tcc caa ggg ggc tgg ggc cac cgg ctg        595
Gln His Cys Gln Gln Asp Arg Ser Gln Gly Gly Trp Gly His Arg Leu
130                     135                     140                     145 gat ggc ttc ccc cct ggg cgg cct tct cca gac aat ctg aac caa atc        643
Asp Gly Phe Pro Pro Gly Arg Pro Ser Pro Asp Asn Leu Asn Gln Ile
                150                     155                     160 tgc ctt cct aac cgt cag cat gtg gta tat ggt ccc tgg aac cta cca        691
Cys Leu Pro Asn Arg Gln His Val Val Tyr Gly Pro Trp Asn Leu Pro
            165                     170                     175 cag tcc agc tac tcc cac ctc act cgc cag ggt gag acc ctc aat ttc        739
Gln Ser Ser Tyr Ser His Leu Thr Arg Gln Gly Glu Thr Leu Asn Phe
        180                     185                     190 ctg gag att gga tat tcc cgc tgc tgc cac tgc cgc agg cac aca aac        787
Leu Glu Ile Gly Tyr Ser Arg Cys Cys His Cys Arg Arg His Thr Asn
    195                     200                     205 cgc cta gag tgt gcc aaa ctt gtg tgg gag gaa gca atg agc cga ttc        835
Arg Leu Glu Cys Ala Lys Leu Val Trp Glu Glu Ala Met Ser Arg Phe
210                     215                     220                     225 tgt gag gcc gag ttc tcg gtc aag acc cga ccc cac tgg tgc tgc acg        883
Cys Glu Ala Glu Phe Ser Val Lys Thr Arg Pro His Trp Cys Cys Thr
                230                     235                     240 cgg cag ggg gag gct cgg ttc tcc tgc ttc cag gag gaa gct ccc cag        931
Arg Gln Gly Glu Ala Arg Phe Ser Cys Phe Gln Glu Glu Ala Pro Gln
            245                     250                     255 cca cac tac cag ctc cgg gcc tgc ccc agc cat cag cct gat att tcc        979
Pro His Tyr Gln Leu Arg Ala Cys Pro Ser His Gln Pro Asp Ile Ser
        260                     265                     270 tcg ggt ctt gag ctg cct ttc cct cct ggg gtg ccc aca ttg gac aat        1027
Ser Gly Leu Glu Leu Pro Phe Pro Pro Gly Val Pro Thr Leu Asp Asn
    275                     280                     285 atc aag aac atc tgc cac ctg agg cgt ttc cgc tct gtg cca cgc aac        1075
Ile Lys Asn Ile Cys His Leu Arg Arg Phe Arg Ser Val Pro Arg Asn
290                     295                     300                     305 ctg cca gct act gac ccc cta caa agg gag ctg ctg gca ctg atc cag        1123
Leu Pro Ala Thr Asp Pro Leu Gln Arg Glu Leu Leu Ala Leu Ile Gln
                310                     315                     320 ctg gag agg gag ttc cag cgc tgc tgc cgc cag ggg aac aat cac acc        1171
Leu Glu Arg Glu Phe Gln Arg Cys Cys Arg Gln Gly Asn Asn His Thr
            325                     330                     335 tgt aca tgg aag gcc tgg gag gat acc ctt gac aaa tac tgt gac cgg        1219
Cys Thr Trp Lys Ala Trp Glu Asp Thr Leu Asp Lys Tyr Cys Asp Arg
        340                     345                     350 gag tat gct gtg aag acc cac cac cac ttg tgt tgc cgc cac cct ccc        1267
Glu Tyr Ala Val Lys Thr His His His Leu Cys Cys Arg His Pro Pro
    355                     360                     365 agc cct act cgg gat gag tgc ttt ggc cgt cgg gct cct tac ccc aac        1315
Ser Pro Thr Arg Asp Glu Cys Phe Gly Arg Arg Ala Pro Tyr Pro Asn
370                     375                     380                     385 tat gac cgg gac atc ttg acc att gac atc ggt cga gtc acc ccc aac        1363
Tyr Asp Arg Asp Ile Leu Thr Ile Asp Ile Gly Arg Val Thr Pro Asn
                390                     395                     400 ctc atg ggc cac ctc tgt gga aac caa aga gtt ctc acc aag cat aaa        1411
```

```
              Leu Met Gly His Leu Cys Gly Asn Gln Arg Val Leu Thr Lys His Lys
                      405                 410                 415 cat att cct ggg ctg atc cac aac atg act gcc cgc tgc tgt gac ctg         1459
His Ile Pro Gly Leu Ile His Asn Met Thr Ala Arg Cys Cys Asp Leu
        420                 425                 430 cca ttt cca gaa cag gcc tgc tgt gca gag gag gag aaa tta acc ttc         1507
Pro Phe Pro Glu Gln Ala Cys Cys Ala Glu Glu Glu Lys Leu Thr Phe
    435                 440                 445 atc aat gat ctg tgt ggt ccc cga cgt aac atc tgg cga gac cct gcc         1555
Ile Asn Asp Leu Cys Gly Pro Arg Arg Asn Ile Trp Arg Asp Pro Ala
450                 455                 460                 465 ctc tgc tgt tac ctg agt cct ggg gat gaa cag gtc aac tgc ttc aac         1603
Leu Cys Cys Tyr Leu Ser Pro Gly Asp Glu Gln Val Asn Cys Phe Asn
                470                 475                 480 atc aat tat ctg agg aac gtg gct cta gtg tct gga gac act gag aac         1651
Ile Asn Tyr Leu Arg Asn Val Ala Leu Val Ser Gly Asp Thr Glu Asn
            485                 490                 495 gcc aag ggc cag ggg gag cag ggc tca act gga gga aca aat atc agc         1699
Ala Lys Gly Gln Gly Glu Gln Gly Ser Thr Gly Gly Thr Asn Ile Ser
        500                 505                 510 tcc acc tct gag ccc aag gaa gaa tgagtcaccc cagagcccta gagggtcaga        1753
Ser Thr Ser Glu Pro Lys Glu Glu
    515                 520 tgggggggaac cccaccctgc ccacccatc tgaacactca ttacactaaa cacctcttgg       1813
aaaaaaaaaa aaaaaaaaa                                                    1832

<210> SEQ ID NO 2
<211> LENGTH: 540
<212> TYPE: PRT
<213> ORGANISM: Homo sapiens

<400> SEQUENCE: 2

Met Gly Thr Thr Ala Arg Ala Ala Leu Val Leu Thr Tyr Leu Ala Val
                -15                 -10                  -5

Ala Ser Ala Ala Ser Glu Gly Gly Phe Thr Ala Thr Gly Gln Arg Gln
     -1   1                   5                  10

Leu Arg Pro Glu His Phe Gln Glu Val Gly Tyr Ala Ala Pro Pro Ser
         15                  20                  25

Pro Pro Leu Ser Arg Ser Leu Pro Met Asp His Pro Asp Ser Ser Gln
 30                  35                  40                  45

His Gly Pro Pro Phe Glu Gly Gln Ser Gln Val Gln Pro Pro Pro Ser
                 50                  55                  60

Gln Glu Ala Thr Pro Leu Gln Gln Glu Lys Leu Leu Pro Ala Gln Leu
             65                  70                  75

Pro Ala Glu Lys Glu Val Gly Pro Pro Leu Pro Gln Glu Ala Val Pro
         80                  85                  90

Leu Gln Lys Glu Leu Pro Ser Leu Gln His Pro Asn Glu Gln Lys Glu
     95                 100                 105

Gly Thr Pro Ala Pro Phe Gly Asp Gln Ser His Pro Glu Pro Glu Ser
110                 115                 120                 125

Trp Asn Ala Ala Gln His Cys Gln Gln Asp Arg Ser Gln Gly Gly Trp
                130                 135                 140

Gly His Arg Leu Asp Gly Phe Pro Pro Gly Arg Pro Ser Pro Asp Asn
            145                 150                 155

Leu Asn Gln Ile Cys Leu Pro Asn Arg Gln His Val Val Tyr Gly Pro
        160                 165                 170
```

```
Trp Asn Leu Pro Gln Ser Ser Tyr Ser His Leu Thr Arg Gln Gly Glu
    175                 180                 185

Thr Leu Asn Phe Leu Glu Ile Gly Tyr Ser Arg Cys Cys His Cys Arg
190                 195                 200                 205

Arg His Thr Asn Arg Leu Glu Cys Ala Lys Leu Val Trp Glu Glu Ala
                210                 215                 220

Met Ser Arg Phe Cys Glu Ala Glu Phe Ser Val Lys Thr Arg Pro His
                225                 230                 235

Trp Cys Cys Thr Arg Gln Gly Glu Ala Arg Phe Ser Cys Phe Gln Glu
            240                 245                 250

Glu Ala Pro Gln Pro His Tyr Gln Leu Arg Ala Cys Pro Ser His Gln
    255                 260                 265

Pro Asp Ile Ser Ser Gly Leu Glu Leu Pro Phe Pro Pro Gly Val Pro
270                 275                 280                 285

Thr Leu Asp Asn Ile Lys Asn Ile Cys His Leu Arg Arg Phe Arg Ser
                290                 295                 300

Val Pro Arg Asn Leu Pro Ala Thr Asp Pro Leu Gln Arg Glu Leu Leu
                305                 310                 315

Ala Leu Ile Gln Leu Glu Arg Glu Phe Gln Arg Cys Cys Arg Gln Gly
            320                 325                 330

Asn Asn His Thr Cys Thr Trp Lys Ala Trp Glu Asp Thr Leu Asp Lys
    335                 340                 345

Tyr Cys Asp Arg Glu Tyr Ala Val Lys Thr His His Leu Cys Cys
350                 355                 360                 365

Arg His Pro Pro Ser Pro Thr Arg Asp Glu Cys Phe Gly Arg Arg Ala
                370                 375                 380

Pro Tyr Pro Asn Tyr Asp Arg Asp Ile Leu Thr Ile Asp Ile Gly Arg
                385                 390                 395

Val Thr Pro Asn Leu Met Gly His Leu Cys Gly Asn Gln Arg Val Leu
            400                 405                 410

Thr Lys His Lys His Ile Pro Gly Leu Ile His Asn Met Thr Ala Arg
    415                 420                 425

Cys Cys Asp Leu Pro Phe Pro Glu Gln Ala Cys Cys Ala Glu Glu Glu
430                 435                 440                 445

Lys Leu Thr Phe Ile Asn Asp Leu Cys Gly Pro Arg Arg Asn Ile Trp
                450                 455                 460

Arg Asp Pro Ala Leu Cys Cys Tyr Leu Ser Pro Gly Asp Glu Gln Val
                465                 470                 475

Asn Cys Phe Asn Ile Asn Tyr Leu Arg Asn Val Ala Leu Val Ser Gly
            480                 485                 490

Asp Thr Glu Asn Ala Lys Gly Gln Gly Glu Gln Gly Ser Thr Gly Gly
    495                 500                 505

Thr Asn Ile Ser Ser Thr Ser Glu Pro Lys Glu Glu
510                 515                 520

<210> SEQ ID NO 3
<211> LENGTH: 31
<212> TYPE: DNA
<213> ORGANISM: Artificial Sequence
<220> FEATURE:
<223> OTHER INFORMATION: Contains a BamHI restriction enzyme site
      followed by nucleotides resembling an efficient signal for the
      initiation of translation in eukaryotic cells just in
      front of the initiation codon for translation

<400> SEQUENCE: 3
```
cgggatccgc catcatgggg accacagcca g							31

<210> SEQ ID NO 4
<211> LENGTH: 26
<212> TYPE: DNA
<213> ORGANISM: Artificial Sequence
<220> FEATURE:
<223> OTHER INFORMATION: Contains the cleavage site for the restriction
      endonuclease XbaI.

<400> SEQUENCE: 4
gctctagatc caagaggtgt ttagtg							26

<210> SEQ ID NO 5
<211> LENGTH: 31
<212> TYPE: DNA
<213> ORGANISM: Artificial Sequence
<220> FEATURE:
<223> OTHER INFORMATION: Contains a BamHI site.

<400> SEQUENCE: 5
gcgcggatcc accatgggga ccacagccag a							31

<210> SEQ ID NO 6
<211> LENGTH: 55
<212> TYPE: DNA
<213> ORGANISM: Artificial Sequence
<220> FEATURE:
<223> OTHER INFORMATION: Contains complementary sequences to an XbaI
      site, translation stop codon, and an HA tag

<400> SEQUENCE: 6
gcgctctaga tcaagcgtag tctgggacgt cgtatgggta ttcttccttg ggctc							55

<210> SEQ ID NO 7
<211> LENGTH: 559
<212> TYPE: PRT
<213> ORGANISM: Mus musculus

<400> SEQUENCE: 7

Met Gly Thr Val Ser Arg Ala Ala Leu Ile Leu Ala Cys Leu Ala Leu
1               5                   10                  15

Ala Ser Ala Ala Ser Glu Gly Ala Phe Lys Ala Ser Asp Gln Arg Glu
            20                  25                  30

Met Thr Pro Glu Arg Leu Phe Gln His Leu His Glu Val Gly Tyr Ala
        35                  40                  45

Ala Pro Pro Ser Leu Pro Gln Thr Arg Arg Leu Arg Val Asp His Ser
    50                  55                  60

Val Thr Ser Leu His Asp Pro Pro Leu Phe Glu Glu Gln Arg Glu Val
65                  70                  75                  80

Gln Pro Pro Ser Ser Pro Glu Asp Ile Pro Val Tyr Glu Glu Asp Trp
                85                  90                  95

Pro Thr Phe Leu Asn Pro Asn Val Asp Lys Ala Gly Pro Ala Val Pro
            100                 105                 110

Gln Glu Ala Ile Pro Leu Gln Lys Glu Gln Pro Pro Gln Val His
        115                 120                 125

Ile Glu Gln Lys Glu Ile Asp Pro Pro Ala Gln Pro Gln Glu Glu Ile
    130                 135                 140

Val Gln Lys Glu Val Lys Pro His Thr Leu Ala Gly Gln Leu Pro Pro
145                 150                 155                 160

Glu Pro Arg Thr Trp Asn Pro Ala Arg His Cys Gln Gln Gly Arg Arg

```
                    165                 170                 175
Gly Val Trp Gly His Arg Leu Asp Gly Phe Pro Pro Gly Arg Pro Ser
            180                 185                 190

Pro Asp Asn Leu Lys Gln Ile Cys Leu Pro Glu Arg Gln His Val Ile
        195                 200                 205

Tyr Gly Pro Trp Asn Leu Pro Gln Thr Gly Tyr Ser His Leu Ser Arg
    210                 215                 220

Gln Gly Glu Thr Leu Asn Val Leu Glu Thr Gly Tyr Ser Arg Cys Cys
225                 230                 235                 240

Pro Cys Arg Ser Asp Thr Asn Arg Leu Asp Cys Leu Lys Leu Val Trp
                245                 250                 255

Glu Asp Ala Met Thr Gln Phe Cys Glu Ala Glu Phe Ser Val Lys Thr
            260                 265                 270

Arg Pro His Leu Cys Cys Arg Leu Arg Gly Glu Glu Arg Phe Ser Cys
        275                 280                 285

Phe Gln Lys Glu Ala Pro Arg Pro Asp Tyr Leu Leu Arg Pro Cys Pro
    290                 295                 300

Val His Gln Asn Gly Met Ser Ser Gly Pro Gln Leu Pro Phe Pro Pro
305                 310                 315                 320

Gly Leu Pro Thr Pro Asp Asn Val Lys Asn Ile Cys Leu Leu Arg Arg
                325                 330                 335

Phe Arg Ala Val Pro Arg Asn Leu Pro Ala Thr Asp Ala Ile Gln Arg
            340                 345                 350

Gln Leu Gln Ala Leu Thr Arg Leu Glu Thr Glu Phe Gln Arg Cys Cys
        355                 360                 365

Arg Gln Gly His Asn His Thr Cys Thr Trp Lys Ala Trp Glu Gly Thr
    370                 375                 380

Leu Asp Gly Tyr Cys Glu Arg Glu Leu Ala Ile Lys Thr His Pro His
385                 390                 395                 400

Ser Cys Cys His Tyr Pro Ser Pro Ala Arg Asp Glu Cys Phe Ala
                405                 410                 415

His Leu Ala Pro Tyr Pro Asn Tyr Asp Arg Asp Ile Leu Thr Leu Asp
            420                 425                 430

Leu Ser Arg Val Thr Pro Asn Leu Met Gly Gln Leu Cys Gly Ser Gly
        435                 440                 445

Arg Val Leu Ser Lys His Lys Gln Ile Pro Gly Leu Ile Gln Asn Met
    450                 455                 460

Thr Val Arg Cys Cys Glu Leu Pro Tyr Pro Glu Gln Ala Cys Cys Gly
465                 470                 475                 480

Glu Glu Lys Leu Ala Phe Ile Glu Asn Leu Cys Gly Pro Arg Arg
                485                 490                 495

Asn Ser Trp Lys Asp Pro Ala Leu Cys Cys Asp Leu Ser Pro Glu Asp
            500                 505                 510

Lys Gln Ile Asn Cys Phe Asn Thr Asn Tyr Leu Arg Asn Val Ala Leu
        515                 520                 525

Val Ala Gly Asp Thr Gly Asn Ala Thr Gly Leu Gly Glu Gln Gly Pro
    530                 535                 540

Thr Arg Gly Thr Asp Ala Asn Pro Ala Pro Gly Ser Lys Glu Glu
545                 550                 555

<210> SEQ ID NO 8
<211> LENGTH: 1457
<212> TYPE: DNA
<213> ORGANISM: Homo sapiens
```

```
<220> FEATURE:
<221> NAME/KEY: CDS
<222> LOCATION: (104)..(1351)
<221> NAME/KEY: sig_peptide
<222> LOCATION: (104)..(160)
<221> NAME/KEY: mat_peptide
<222> LOCATION: (161)..(1348)

<400> SEQUENCE: 8
```

| | |
|---|---:|
| acaaccgtaa cagccaccag acaagcttca gtggccggcc cttcacatcc agacttgcct | 60 |
| gagaggaccc acctctgagt gtccagtggt cagttgcccc agg atg ggg acc aca<br>                                                                               Met Gly Thr Thr | 115 |
| gcc aga gca gcc ttg gtc ttg acc tat ttg gct gtt gct tct gct gcc<br>Ala Arg Ala Ala Leu Val Leu Thr Tyr Leu Ala Val Ala Ser Ala Ala<br>-15                  -10                -5                    -1 1 | 163 |
| tct gag gga ggc ttc acg gct aca gga cag agg cag ctg agg cca gag<br>Ser Glu Gly Gly Phe Thr Ala Thr Gly Gln Arg Gln Leu Arg Pro Glu<br>            5                        10                        15 | 211 |
| cac ttt caa gaa gtt ggc tac gca gct ccc ccc tcc cca ccc cta tcc<br>His Phe Gln Glu Val Gly Tyr Ala Ala Pro Pro Ser Pro Pro Leu Ser<br>        20                        25                        30 | 259 |
| cga agc ctc ccc atg gat cac cct gac tcc tct cag cat ggc cct ccc<br>Arg Ser Leu Pro Met Asp His Pro Asp Ser Ser Gln His Gly Pro Pro<br>35                    40                        45 | 307 |
| ttt gag gga cag agt caa gtg cag ccc cct ccc tct cag gag gcc acc<br>Phe Glu Gly Gln Ser Gln Val Gln Pro Pro Pro Ser Gln Glu Ala Thr<br>50                    55                        60                        65 | 355 |
| cct ctc caa cag gaa aag ctg cta cct gcc caa ctc cct gct gaa aag<br>Pro Leu Gln Gln Glu Lys Leu Leu Pro Ala Gln Leu Pro Ala Glu Lys<br>                70                        75                        80 | 403 |
| gaa gtg ggt ccc cct ctc cct cag gaa gct gtc ccc ctc caa aaa gag<br>Glu Val Gly Pro Pro Leu Pro Gln Glu Ala Val Pro Leu Gln Lys Glu<br>                  85                        90                        95 | 451 |
| ctg ccc tct ctc cag cac ccc aat gaa cag aag gaa gga acg cca gct<br>Leu Pro Ser Leu Gln His Pro Asn Glu Gln Lys Glu Gly Thr Pro Ala<br>                100                     105                     110 | 499 |
| cca ttt ggg gac cag agc cat cca gaa cct gag tcc tgg aat gca gcc<br>Pro Phe Gly Asp Gln Ser His Pro Glu Pro Glu Ser Trp Asn Ala Ala<br>115                     120                     125 | 547 |
| cag cac tgc caa cag gac cgg tcc caa ggg ggc tgg ggc cac cgg ctg<br>Gln His Cys Gln Gln Asp Arg Ser Gln Gly Gly Trp Gly His Arg Leu<br>130                  135                    140                  145 | 595 |
| gat ggc ttc ccc cct ggg cgg cct tct cca gac aat ctg aac caa atc<br>Asp Gly Phe Pro Pro Gly Arg Pro Ser Pro Asp Asn Leu Asn Gln Ile<br>                150                     155                     160 | 643 |
| tgc ctt cct aac cgt cag cat gtg gta tat ggt ccc tgg aac cta cca<br>Cys Leu Pro Asn Arg Gln His Val Val Tyr Gly Pro Trp Asn Leu Pro<br>                  165                     170                     175 | 691 |
| cag tcc agc tac tcc cac ctc act cgc cag ggt gag acc ctc aat ttc<br>Gln Ser Ser Tyr Ser His Leu Thr Arg Gln Gly Glu Thr Leu Asn Phe<br>              180                     185                     190 | 739 |
| ctg gag att gga tat tcc cgc tgc tgc cac tgc cgc agg cac aca aac<br>Leu Glu Ile Gly Tyr Ser Arg Cys Cys His Cys Arg Arg His Thr Asn<br>195                     200                     205 | 787 |
| cgc cta gag tgt gcc aaa ctt gtg tgg gag gat acc ctt gac aaa tac<br>Arg Leu Glu Cys Ala Lys Leu Val Trp Glu Asp Thr Leu Asp Lys Tyr<br>210                   215                    220                  225 | 835 |
| tgt gac cgg gag tat gct gtg aag acc cac cac cac ttg tgt tgc cgc<br>Cys Asp Arg Glu Tyr Ala Val Lys Thr His His His Leu Cys Cys Arg<br>                230                     235                     240 | 883 |

```
                          -continued cac cct ccc agc cct act cgg gat gag tgc ttt ggc cgt cgg gct cct      931
His Pro Pro Ser Pro Thr Arg Asp Glu Cys Phe Gly Arg Arg Ala Pro
            245                 250                 255 tac ccc aac tat gac cgg gac atc ttg acc att gac atc ggt cga gtc      979
Tyr Pro Asn Tyr Asp Arg Asp Ile Leu Thr Ile Asp Ile Gly Arg Val
        260                 265                 270 acc ccc aac ctc atg ggc cac ctc tgt gga aac caa aga gtt ctc acc     1027
Thr Pro Asn Leu Met Gly His Leu Cys Gly Asn Gln Arg Val Leu Thr
    275                 280                 285 aag cat aaa cat att cct ggg ctg atc cac aac atg act gcc cgc tgc     1075
Lys His Lys His Ile Pro Gly Leu Ile His Asn Met Thr Ala Arg Cys
290                 295                 300                 305 tgt gac ctg cca ttt cca gaa cag gcc tgc tgt gca gag gag gag aaa     1123
Cys Asp Leu Pro Phe Pro Glu Gln Ala Cys Cys Ala Glu Glu Glu Lys
                310                 315                 320 tta acc ttc atc aat gat ctg tgt ggt ccc cga cgt aac atc tgg cga     1171
Leu Thr Phe Ile Asn Asp Leu Cys Gly Pro Arg Arg Asn Ile Trp Arg
            325                 330                 335 gac cct gcc ctc tgc tgt tac ctg agt cct ggg gat gaa cag gtc aac     1219
Asp Pro Ala Leu Cys Cys Tyr Leu Ser Pro Gly Asp Glu Gln Val Asn
        340                 345                 350 tgc ttc aac atc aat tat ctg agg aac gtg gct cta gtg tct gga gac     1267
Cys Phe Asn Ile Asn Tyr Leu Arg Asn Val Ala Leu Val Ser Gly Asp
    355                 360                 365 act gag aac gcc aag ggc cag ggg gag cag ggc tca act gga gga aca     1315
Thr Glu Asn Ala Lys Gly Gln Gly Glu Gln Gly Ser Thr Gly Gly Thr
370                 375                 380                 385 aat atc agc tcc acc tct gag ccc aag gaa gaa tgagtcaccc cagagcccta   1368
Asn Ile Ser Ser Thr Ser Glu Pro Lys Glu Glu
                390                 395 gagggtcaga tggggggaac cccaccctgc cccacccatc tgaacactca ttacactaaa   1428
cacctcttgg aaaaaaaaaa aaaaaaaaa                                     1457

<210> SEQ ID NO 9
<211> LENGTH: 415
<212> TYPE: PRT
<213> ORGANISM: Homo sapiens

<400> SEQUENCE: 9

Met Gly Thr Thr Ala Arg Ala Ala Leu Val Leu Thr Tyr Leu Ala Val
                -15                 -10                  -5

Ala Ser Ala Ala Ser Glu Gly Gly Phe Thr Ala Thr Gly Gln Arg Gln
     -1   1               5                  10

Leu Arg Pro Glu His Phe Gln Glu Val Gly Tyr Ala Ala Pro Pro Ser
         15                 20                  25

Pro Pro Leu Ser Arg Ser Leu Pro Met Asp His Pro Asp Ser Ser Gln
30                  35                  40                  45

His Gly Pro Pro Phe Glu Gly Gln Ser Gln Val Gln Pro Pro Ser
             50                  55                  60

Gln Glu Ala Thr Pro Leu Gln Gln Glu Lys Leu Leu Pro Ala Gln Leu
             65                  70                  75

Pro Ala Glu Lys Glu Val Gly Pro Pro Leu Pro Gln Glu Ala Val Pro
         80                  85                  90

Leu Gln Lys Glu Leu Pro Ser Leu Gln His Pro Asn Glu Gln Lys Glu
     95                 100                 105

Gly Thr Pro Ala Pro Phe Gly Asp Gln Ser His Pro Glu Pro Glu Ser
110                 115                 120                 125
```

-continued

```
Trp Asn Ala Ala Gln His Cys Gln Gln Asp Arg Ser Gln Gly Gly Trp
            130                 135                 140

Gly His Arg Leu Asp Gly Phe Pro Pro Gly Arg Pro Ser Pro Asp Asn
            145                 150                 155

Leu Asn Gln Ile Cys Leu Pro Asn Arg Gln His Val Val Tyr Gly Pro
            160                 165                 170

Trp Asn Leu Pro Gln Ser Ser Tyr Ser His Leu Thr Arg Gln Gly Glu
    175                 180                 185

Thr Leu Asn Phe Leu Glu Ile Gly Tyr Ser Arg Cys Cys His Cys Arg
190                 195                 200                 205

Arg His Thr Asn Arg Leu Glu Cys Ala Lys Leu Val Trp Glu Asp Thr
                210                 215                 220

Leu Asp Lys Tyr Cys Asp Arg Glu Tyr Ala Val Lys Thr His His His
            225                 230                 235

Leu Cys Cys Arg His Pro Pro Ser Pro Thr Arg Asp Glu Cys Phe Gly
            240                 245                 250

Arg Arg Ala Pro Tyr Pro Asn Tyr Asp Arg Asp Ile Leu Thr Ile Asp
    255                 260                 265

Ile Gly Arg Val Thr Pro Asn Leu Met Gly His Leu Cys Gly Asn Gln
270                 275                 280                 285

Arg Val Leu Thr Lys His Lys His Ile Pro Gly Leu Ile His Asn Met
            290                 295                 300

Thr Ala Arg Cys Cys Asp Leu Pro Phe Pro Glu Gln Ala Cys Cys Ala
            305                 310                 315

Glu Glu Glu Lys Leu Thr Phe Ile Asn Asp Leu Cys Gly Pro Arg Arg
            320                 325                 330

Asn Ile Trp Arg Asp Pro Ala Leu Cys Cys Tyr Leu Ser Pro Gly Asp
    335                 340                 345

Glu Gln Val Asn Cys Phe Asn Ile Asn Tyr Leu Arg Asn Val Ala Leu
350                 355                 360                 365

Val Ser Gly Asp Thr Glu Asn Ala Lys Gly Gln Gly Glu Gln Gly Ser
            370                 375                 380

Thr Gly Gly Thr Asn Ile Ser Ser Thr Ser Glu Pro Lys Glu Glu Glu
            385                 390                 395
```

What is claimed is:

1. An isolated polypeptide comprising an amino acid sequence selected from the group consisting of:
   (a) amino acid residues −19 to 521 of SEQ ID NO:2;
   (b) amino acid residues −18 to 521 of SEQ ID NO:2; and
   (c) amino acid residues 1 to 521 of SEQ ID NO:2.

2. The isolated polypeptide of claim 1 which comprises amino acid sequence (a).

3. The isolated polypeptide of claim 1 which comprises amino acid sequence (b).

4. The isolated polypeptide of claim 1 which comprises amino acid sequence (c).

5. The isolated polypeptide of claim 1 wherein the isolated polypeptide further comprises a heterologous polypeptide.

6. The isolated polypeptide of claim 1 wherein said isolated polypeptide is glycosylated.

7. The isolated polypeptide of claim 1 wherein said isolated polypeptide is fused to polyethylene glycol.

8. An isolated polypeptide produced by a method comprising:
   (a) expressing the polypeptide of claim 1 by a cell; and
   (b) recovering the polypeptide.

9. A composition comprising the isolated polypeptide of claim 1 and a earner.

10. An isolated polypeptide comprising an amino acid sequence selected from the group consisting of:
    (a) the amino acid sequence of the full-length polypeptide encoded by the cDNA in ATCC Deposit No. 97302;
    (b) the amino acid sequence of the full-length polypeptide, excluding the N-terminal methionine residue, encoded by the cDNA in ATCC Deposit No. 97302; and
    (c) the amino acid sequence of the mature polypeptide encoded by the cDNA in ATCC Deposit No. 97302.

11. The isolated polypeptide of claim 10 which comprises amino acid sequence (a).

12. The isolated polypeptide of claim 10 which comprises amino acid sequence (b).

13. The isolated polypeptide of claim 10 which comprises amino acid sequence (c).

14. The isolated polypeptide of claim 10 wherein the isolated polypeptide further comprises a heterologous polypeptide.

15. The isolated polypeptide of claim 10 wherein said isolated polypeptide is glycosylated.

16. The isolated polypeptide of claim 10 wherein said isolated polypeptide is fused to polyethylene glycol.

17. An isolated polypeptide produced by a method comprising:
(a) expressing the polypeptide of claim 10 by a cell; and
(b) recovering the polypeptide.

18. A composition comprising the isolated polypeptide of claim 10 and a carrier.

19. An isolated first polypeptide at least 90% identical to a second polypeptide selected from the group consisting of:
(a) amino acid residues −19 to 521 of SEQ ID NO:2;
(b) amino acid residues −18 to 521 of SEQ ID NO:2; and
(c) amino acid residues 1 to 521 of SEQ ID NO:2,
wherein the first polypeptide stimulates wound healing.

20. The isolated first polypeptide of claim 19 wherein the second polypeptide is (a).

21. The isolated first polypeptide of claim 19 wherein the second polypeptide is (b).

22. The isolated first polypeptide of claim 19 wherein the second polypeptide is (c).

23. The isolated first polypeptide of claim 19 wherein the first polypeptide is at least 95% identical to the second polypeptide (a).

24. The isolated first polypeptide of claim 19 wherein the first polypeptide is at least 95% identical to the second polypeptide (b).

25. The isolated first polypeptide of claim 19 wherein the first polypeptide is at least 95% identical to the second polypeptide (c).

26. The isolated first polypeptide of claim 19 wherein the first polypeptide further comprises a heterologous polypeptide.

27. The isolated first polypeptide of claim 19 wherein said isolated first polypeptide is glycosylated.

28. The protein of claim 19 wherein said isolated first polypeptide is fused to polyethylene glycol.

29. An isolated polypeptide produced by a method comprising:
(a) expressing the first polypeptide of claim 19 by a cell; and
(b) recovering the first polypeptide.

30. A composition comprising the isolated first polypeptide of claim 19 and a carrier.

31. An isolated first polypeptide at least 90% identical to a second polypeptide selected from the group consisting of:
(a) the amino acid sequence of the full-length polypeptide encoded by the cDNA in ATCC Deposit No. 97302;
(b) the amino acid sequence of the full-length polypeptide, excluding the N-terminal methionine residue, encoded by the cDNA in ATCC Deposit No. 97302; and
(c) the amino acid sequence of the mature polypeptide encoded by the cDNA in ATCC Deposit No. 97302,
wherein the first polypeptide stimulates wound healing.

32. The isolated first polypeptide of claim 31 wherein the second polypeptide is (a).

33. The isolated first polypeptide of claim 31 wherein the second polypeptide is (b).

34. The isolated first polypeptide of claim 31 wherein the second polypeptide is (c).

35. The isolated first polypeptide of claim 31 wherein the first polypeptide is at least 95% identical to the second polypeptide (a).

36. The isolated first polypeptide of claim 31 wherein the first polypeptide is at least 95% identical to the second polypeptide (b).

37. The isolated first polypeptide of claim 31 wherein the first polypeptide is at least 95% identical to the second polypeptide (c).

38. The isolated first polypeptide of claim 31 wherein the first polypeptide further comprises a heterologous polypeptide.

39. The isolated first polypeptide of claim 31 wherein said isolated first polypeptide is glycosylated.

40. The protein of claim 31 wherein said isolated first polypeptide is fused to polyethylene glycol.

41. An isolated polypeptide produced by a method comprising:
(a) expressing the first polypeptide of claim 31 by a cell; and
(b) recovering the first polypeptide.

42. A composition comprising the isolated first polypeptide of claim 31 and a carrier.

43. An isolated polypeptide comprising an amino acid sequence selected from the group consisting of:
(a) a fragment of amino acid residues 1 to 521 of SEQ ID NO:2, wherein the fragment stimulates osteogenesis;
(b) a fragment of amino acid residues 1 to 521 of SEQ ID NO:2, wherein the fragment stimulates angiogenesis;
(c) a fragment of the full-length polypeptide encoded by the cDNA in ATCC Deposit No. 97302, wherein the fragment stimulates osteogenesis; and
(d) a fragment of the full-length polypeptide encoded by the cDNA in ATCC Deposit No. 97302, wherein the fragment stimulates angiogenesis.

44. The isolated polypeptide of claim 43 which comprises amino acid sequence (a).

45. The isolated polypeptide of claim 43 which comprises amino acid sequence (b).

46. The isolated polypeptide of claim 43 which comprises amino acid sequence (c).

47. The isolated polypeptide of claim 43 which comprises amino acid sequence (d).

48. The isolated polypeptide of claim 43 wherein the isolated polypeptide further comprises a heterologous polypeptide.

49. The isolated polypeptide of claim 43 wherein said isolated polypeptide is glycosylated.

50. The isolated polypeptide of claim 43 said isolated polypeptide is fused to polyethylene glycol.

51. An isolated polypeptide produced by a method comprising:
(a) expressing the polypeptide of claim 43 by a cell; and
(b) recovering the polypeptide.

52. A composition comprising the isolated polypeptide of claim 43 and a carrier.

53. An isolated polypeptide consisting of at least 30 contiguous amino acid residues of SEQ ID NO:2.

54. The isolated polypeptide of claim 53 wherein the isolated polypeptide consists of at least 50 contiguous amino acid residues of SEQ ID NO:2.

55. The isolated polypeptide of claim 53 wherein the isolated polypeptide stimulates osteogenesis.

56. The isolated polypeptide of claim 53 wherein the isolated polypeptide stimulates angiogenesis.

57. The isolated polypeptide of claim 53 wherein the isolated polypeptide further comprises a heterologous polypeptide.

58. The isolated polypeptide of claim 53 wherein said isolated polypeptide is glycosylated.

59. The isolated polypeptide of claim 53 wherein said isolated polypeptide is fused to polyethylene glycol.

60. An isolated polypeptide produced by a method comprising:
   (a) expressing the polypeptide of claim 53 by a cell; and
   (b) recovering the polypeptide.

61. A composition comprising the isolated polypeptide of claim 53 and a carrier.

62. An isolated polypeptide consisting of at least 30 contiguous amino acid residues encoded by the cDNA in ATCC Deposit No. 97302.

63. The isolated polypeptide of claim 62 wherein the isolated polypeptide consists of at least 50 contiguous amino acid residues encoded by the cDNA in ATCC No. 97302.

64. The isolated polypeptide of claim 62 wherein the isolated polypeptide stimulates osteogenesis.

65. The isolated polypeptide of claim 62 wherein the isolated polypeptide stimulates angiogenesis.

66. The isolated polypeptide of claim 62 wherein the isolated polypeptide further comprises a heterologous polypeptide.

67. The isolated polypeptide of claim 62 wherein said isolated polypeptide is glycosylated.

68. The isolated polypeptide of claim 62 wherein said isolated polypeptide is fused to polyethylene glycol.

69. An isolated polypeptide produced by a method comprising:
   (a) expressing the polypeptide of claim 62 by a cell; and
   (b) recovering the polypeptide.

70. A composition comprising the isolated polypeptide of claim 62 and a carrier.

* * * * *